United States Patent [19]

Stern et al.

[11] Patent Number: 6,013,817

[45] Date of Patent: *Jan. 11, 2000

[54] PROCESS FOR THE PRODUCTION OF ETHYL ESTERS

[75] Inventors: Robert Stern, Paris; Gerard Hillion, Herblay, both of France; Mohammed Neguib Eisa, Vienne, Austria

[73] Assignee: Institut Francais du Petrole, Rueil Malmaison, France

[ * ] Notice: This patent issued on a continued prosecution application filed under 37 CFR 1.53(d), and is subject to the twenty year patent term provisions of 35 U.S.C. 154(a)(2).

[21] Appl. No.: 08/852,737

[22] Filed: May 7, 1997

[30] Foreign Application Priority Data

May 7, 1996 [FR] France .................................. 96 05820

[51] Int. Cl.⁷ .................................................. C07C 51/00
[52] U.S. Cl. ............................................................ 554/167
[58] Field of Search ............................................. 554/167

[56] References Cited

U.S. PATENT DOCUMENTS

| | | | |
|---|---|---|---|
| 4,608,202 | 8/1986 | Lepper et al. | 554/167 |
| 4,695,411 | 9/1987 | Stern et al. | 554/167 |
| 5,354,878 | 10/1994 | Connemann et al. | 554/167 |

FOREIGN PATENT DOCUMENTS

| | | |
|---|---|---|
| 626014 | 7/1992 | Australia . |
| 94/17027 | 8/1994 | WIPO . |

OTHER PUBLICATIONS

Lago et al., "Extraction and transesterification of vegetable oils with ethanol", *Oleagineaux*, 140(30:147–151, Mar. 1985.

*Primary Examiner*—Paul J. Killos
*Assistant Examiner*—J. Parsa
*Attorney, Agent, or Firm*—Millen, White, Zelano & Branigan, P.C.

[57] ABSTRACT

For the production of ethyl esters of fatty acids from fatty acid glycerides such as vegetable or animal oil or fat or other mixtures of glycerides, the process comprises the following stages: (a) transesterifying fatty acid glycerides with hydrated ethyl alcohol using an alkaline catalyst to form a medium comprising ethyl esters and excess ethyl alcohol; (b) adding a glycerine phase to said medium, and evaporating the excess ethyl alcohol to produce two immiscible phases, an ester phase and a glycerine phase A, and recycling said excess ethyl alcohol to stage (a); (c) separating said glycerine phase A and said ester phase to obtain the desired ethyl esters; (d) neutralizing said glycerine phase A with acid, and separating resultant "fatty acids+esters" phase and a glycerine phase B, and drying the latter phase; (e) subjecting the "fatty acids+esters" phase to glycerolysis with at least a fraction of the dried glycerine phase B in the presence of an alkaline catalyst to form a mixture of glycerides and esters, and passing said mixture into transesterification stage (a).

18 Claims, 1 Drawing Sheet

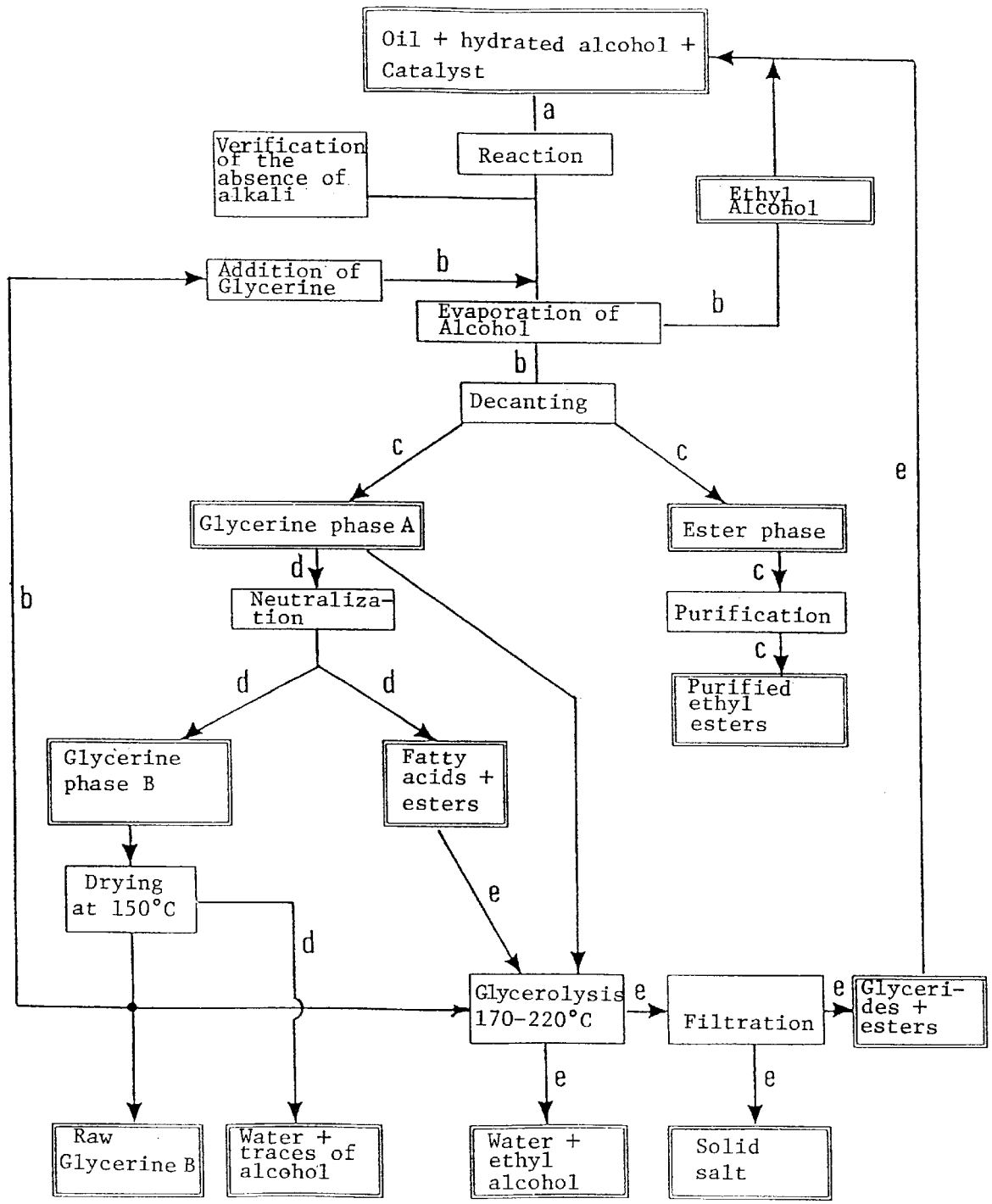

PROCESS FOR THE PRODUCTION OF ETHYL ESTERS

BACKGROUND OF THE INVENTION

The invention relates to a new process for the production of ethyl esters that are derived from natural fatty substances, whereby these esters can be used particularly as fuels for diesel engines or as household fuels.

Numerous processes for producing esters that use dry ethyl alcohol are known. In general, these processes are similar to those that use methyl alcohol, except that the ethyl alcohol sometimes has to be evaporated before the glycerine is decanted. Furthermore, while a great deal of literature is devoted to the drying of ethyl alcohol, it is still a fact that the recommended processes are often expensive, especially on a small scale. On a large scale (i.e., several thousand tons/year), the operating expenses may be small, but the investments are very large.

In the field of transesterification of fatty substances with hydrated alcohols (in particular hydrated ethyl alcohol), there are very few references. For example, French Patent FR-B-2,577,569, in the name of the same assignee, describes the use of acid catalysts, but the reaction is completed first by drying the ethyl alcohol in an operation aimed at esterifying the free acid and then by a step using basic catalysis. In the alcohol drying operation, a molecular sieve is used that has to be regenerated.

Under these conditions, the production of ethyl esters of fatty substances by means of hydrated ethyl alcohol does not appear to be cost effective on a relatively small industrial because it is desired to obtain a fairly pure ethyl ester in a good yield relative to the staring fatty substances, while allowing for the possibility of recycling excess alcohol with relative simplicity.

SUMMARY OF THE INVENTION

It has now been discovered, unexpectedly, that by combining several known stages separately, it was possible to reach the desired goal, i.e., to reconcile the various requirements imposed on a process that has to be usable on a small scale. Among these requirements, an investment that must remain small can be mentioned, in connection particularly with the metal components of the equipment that is used (steel structures) and the need to resort to vacuum or to pressurized operations as little as possible.

The principle of the process of the invention lies in the fact that the excess ethyl alcohol that is used to ensure good conversion of glyceride esters of the treated oil can be recycled despite a concentration of water that is greater than that of the starting alcohol. This is made possible by the addition of glycerine, which acts as a desiccant, in that more water is retained than alcohol. The losses of ethyl esters that are entrained by the glycerine with the soaps that are formed are compensated for by recycling of the phase of "esters+ fatty acids" which are partially retransformed into glyceride.

Thus, the invention proposes a process for the production of ethyl esters of fatty acids from vegetable and/or animal oil or fat or other glyceride mixtures, whereby this process can be defined in general by the fact that it comprises five stages as defined below, in connection with the diagram that will be presented below.

In a stage (a), the oil, the fat, or the starting glyceride mixture is transesterified by excess hydrated ethyl alcohol using an alkaline catalyst.

In a stage (b), a glycerine phase, which can be a fraction of dried glycerine phase B that is obtained in stage (d) below, is added to the medium, and the excess ethyl alcohol is evaporated to produce two immiscible phases, an ester phase and a glycerine phase A, and the excess ethyl alcohol is recycled to stage (a).

In a stage (c), said glycerine phase A and said ester phase, which is purified, are separated to obtain the ethyl esters that are desired.

In a stage (d), said glycerine phase A is neutralized, and a "fatty acids and esters" phase and a glycerine phase B, which is dried, are separated, whereby a dried fraction of glycerine phase B can be returned to stage (b).

In a stage (e), the glycerolysis of the "fatty acids+esters" phase is carried out with a fraction of dried glycerine phase B and in the presence of an alkaline catalyst, which can be a fraction of glycerine phase A, to form, after separation, for example, by filtration, a mixture of glycerides and esters, which is sent into a transesterification stage such as (a).

DESCRIPTION OF DRAWING

The attached drawing is a self-explanatory block flow-sheet of a preferred comprehensive embodiment of the invention.

The various stages of the process of the invention are described in more detail below.

In stage (a), it is advantageous to start with a neutral oil so as not to increase the consumption of alkaline catalyst, which is already greater than when the procedure is performed with a dry alcohol. The oils and fats that can be used in the process of the invention are generally all natural (vegetable or animal) oils that are known in the fields of food and industry. As examples, lauric oils (copra and cabbage palm oils), palmitic-acid-rich oils (palm and tallow oil), oleic-acid-rich oils (peanut, rapeseed, and olive oils), polyunsaturated acid-rich oils (fish, soybean, linseed, nut, safflower, and sunflower seed oils), etc., can be cited. If it is desired to use waste kitchen oils, which are overly acidic, it is first necessary to reduce their acidity by glycerolysis at a temperature of 60 to 100° C. in the presence of an acid catalyst and glycerine.

With the transesterification of stage (a) being carried out under basic catalysis, the water content of the ethyl alcohol used plays a big role in the conversion of the oil. Actually, the higher the water content, the more difficult it is to obtain an ethyl ester with good purity at the end of stage (c). There is competition between the transesterification, which requires an alkaline alcoholate as a catalyst, and saponification, which transforms the catalyst into soap. The presence of water promotes the saponification of the oil or ethyl esters. Also, the ethyl alcohol that is used generally will exhibit a pure alcohol level of 92 to 99%, most often 94 to 97%. It is actually possible to exceed the azeotropic concentration of 96%. Thanks to the presence of glycerine in stage (b), which comprises evaporation of excess ethyl alcohol, the ethyl alcohol that moves to the top is drier than the starting alcohol, and it is possible to recycle it with no problem to stage (a). It is also possible to consider adding to ethyl alcohol another alcohol, with methyl alcohol being particularly advantageous in this connection, since it makes possible better conversion in a basic medium and in addition it is a denaturing component.

Generally a proportion of ethyl alcohol of 30 to 100%, preferably 40 to 60%, by weight is used relative to the starting oil. Under these conditions, to obtain total conversion of the oil, it is appropriate to use a proportion of alkaline catalyst, expressed in terms of weight of soda, of 1 to 2% by weight relative to the starting oil. The catalyst can be selected from among, for example, soda, potash, and alcoholates of sodium or potassium, such as, for example, sodium methylate or sodium ethylate. Soda is preferably used because of its low cost. It may also be advantageous to use potash when glycerine phase A, in stage (d), is neutralized with phosphoric acid. In this case, the glycerine phase will contain potassium phosphate that can be separated from glycerine and used as, for example, fertilizer. This separation could be done after the drying stage by, for example, filtration of the salt.

The temperature employed to implement the transesterification reaction, in the presence of an alkaline catalyst, can range from, for example, 5 to 120° C. It is convenient, however, to work between 20 and 50° C. If it is desired to save a reactor, it is possible to carry out the reaction in a simple storage tank, provided that stirring can be carried out for at least several minutes until a homogenous phase is obtained. At temperatures of 5 to 8° C., it is possible, for some concentrations of ethyl alcohol, to obtain two phases and to wind up, with less than 1% by weight of catalyst, with total conversion of the oil into ester (minus what is transformed into soaps). This does not necessarily involve a very advantageous weight balance, however, because a portion of the ethyl ester remains in the glycerine phase. In contrast, starting at 15–20° C., a single phase is generally obtained, primarily when more than 40% by weight of ethyl alcohol is used relative to the starting oil. The higher temperatures promote saponification rather than transesterification. A loss of ethyl esters arises from the fact that when a glycerine phase is formed—whatever the conditions may be, which are, however, still basic—the soaps entrain a large amount of esters in the latter. This is only an apparent loss, however, since these esters will later be recovered and recycled in the process.

The reaction time depends on temperature. It can vary between, for example, 30 minutes and 24 hours. Most often, 80% conversion is obtained at the end of several minutes and sometimes 97% after several hours. In general, it is not effective to add the catalyst several times in the absence of intermediate decanting.

In stage (b) of the process of the invention, the glycerine phase that is added is advantageously a fraction of glycerine phase B that is produced in phase (d), after drying, except, of course, for treating the first batch, for which a commercial glycerine, for example of 90% purity, is used.

The amount of glycerine that is added in stage (b) depends on the amount of ethyl alcohol that is involved in stage (a). In general, however, 20 to 40% by weight of glycerine is added relative to the starting oil, particularly when this is a predominantly oleic oil or another oil that contains primarily fatty acids with 18 carbon atoms.

Before the glycerine phase is added, in stage (b), it is advantageous to verify, in some cases, that there is no strong base in the reaction medium. Actually, the presence of a strong base would cause the reverse reaction of transesterification of ethyl ester by glycerine to re-form glycerides. The determination of this basicity can be done easily with a pH-meter.

The evaporation of the ethyl alcohol, after glycerine is added to stage (b), can be done at atmospheric pressure with a distilling column that has a small number of plates (for example 1 to 5), or at reduced pressure. In distillation, the first drops are anhydrous ethyl alcohol. In general, distillation is halted when 70 to 90% of the excess ethyl alcohol committed has been collected. It is necessary to ensure, by a suitable method, that the percentage of alcohol that is thus recovered is not less than that of the alcohol that is committed initially. Under these conditions, the alcohol that is recovered can be recycled to the start of transesterification stage (a).

In stage (c) of the process of the invention, the decanting of the two phases that are obtained at the end of stage (b) is preferably done at high temperature, for example about 75° C. At such a temperature, 30 minutes is sufficient to make the two phases clear. The ester phase, which is the upper phase, is separated and subjected to purification by standard means, such as those described in, for example, Patent FR-B-2,635,520. It is possible to proceed by adding 1 to 2% by weight of water, then acidulous water and again water; or by sending the material over an ion exchange resin or activated earth and evaporation; or by combining various techniques.

In stage (d), glycerine phase A is treated to facilitate the recycling of fatty substances (esters and acids) that are entrained in the latter. The soaps that are present in said glycerine phase are neutralized by a solution of strong mineral acid, for example, sulfuric, hydrochloric, or phosphoric acid. This latter acid makes it possible to avoid problems of equipment corrosion. Two phases are formed: the upper phase consists of a mixture of fatty acids and esters, and the lower phase is glycerine phase B, which also contains traces of alcohol, water, and the mineral salts that are formed with the acid that is used. The two phases decant easily, in general at a temperature of 30 to 50° C. The pH of glycerine solution B is in general from 5 to 6. A small fraction of glycerine phase A can be put aside to be used as catalyst in subsequent stage (e) of glycerolysis of separated esters and fatty acids. Depending on the dilution of sulfuric or phosphoric acid, it is also possible to obtain, immediately after neutralization, a solid phase of salts that can be filtered before decanting.

In stage (e), the fatty acids and optionally a portion of the esters are transformed into glycerides by glycerolysis by means of glycerine, which can be a fraction of glycerine phase B that is separated during preceding stage (d) and dried at a temperature, for example, that can range up to about 170° C. The glycerolysis is carried out in the presence of an alkaline catalyst, which can advantageously consist of a fraction of glycerine phase A (which is alkaline since it contains soaps), used at a concentration that is generally equivalent to 0.1 to 0.2% by weight of soda, relative to the "fatty acids+esters" phase. In this glycerolysis stage, it is generally not necessary to use large amounts of neutral glycerine and alkaline glycerine, the goal of the operation being only to reduce the acidity of the "fatty acids+esters" mixture and to transform it into glycerides. The glycerolysis reaction is generally carried out in a reactor that is equipped with an evaporator and a condenser to recover the water and alcohol that are present. The reaction starts at about 170° C. and can be advantageously taken to a temperature of 180 to 220° C. to obtain an acid number that is less than 2. The duration of the reaction depends on the amount of fatty acids that is initially present. The reaction can be carried out under a slight vacuum. The final product is generally made of two phases: a liquid phase which is a mixture of glycerides and esters and a solid phase which consists of salts and traces of soaps. The latter is filtered with the addition of a small amount of ethyl alcohol, if necessary.

The glycerolysis reaction can be implemented continuously with three reactors in series. This reaction has already been described, for example, in French Patent FR-B-2,696,185.

If their acidity is reduced to an acid number that is less than 2, there is no reason why—except sometimes their color—the glycerides thus formed cannot be used as is as the sole raw material in a new production of esters. It is advantageous, however, to mix them with the staring oil by returning to stage (a) of the process of the invention. In view of the fact that the "acid+esters" phase that is recovered and treated by glycerolysis in general represents 15 to 20% by weight of the stating batch to be transesterified, if it is assumed that, in practice, a reactor of the same capacity is used for glycerolysis and for transesterification, it will be necessary to perform a glycerolysis treatment each time that about five to seven transesterification operations are performed. In connection with the results of the process of the invention, it is possible to obtain between 100 and 105% by weight of ethyl esters relative to the starting oil. Losses are therefore negligible.

During the process, water is eliminated and/or separated at three stages. First, in stage (b), when the alcohol is evaporated by obtaining an azeotrope or even enriched alcohol; then in stage (d), when glycerine phase B is dried; finally in stage (e), during glycerolysis.

If a balance of the glycerine in the process is drawn up, it is possible to identify four glycerine flows. Three flows come from dried glycerine phase B: one which is recycled to improve the decanting of the reaction medium after the transesterification reaction in stage (b); one that is sent to the glycerolysis of stage (e); and a majority fraction that is removed from the process. A fourth glycerine flow is the one that comes from glycerine phase A, which can be used to bring the basic catalyst into glycerolysis.

If the balance of ethyl alcohol is taken into consideration, it is noted that the proportion of alcohol that is lost during the process is small because the glycerine, in stage (b), makes it possible to recover an alcohol that is not very hydrated, with the presence of glycerine having the effect of inhibiting the evaporation of water, and therefore promoting the evaporation of the alcohol.

Furthermore, the "water+alcohol" mixture that is recovered during the drying of glycerine B in stage (d) and/or after glycerolysis in stage (e) can be used in, for example, washing ion-exchange resins that can be used to purify the ester that is obtained at the end of phase (c).

The following examples illustrate the invention.

EXAMPLE 1

Production of ethyl esters of sunflower seed oil.

In a first stage, 1000 g of neutralized sunflower seed oil, 500 g of ethyl alcohol at 95% by weight of alcohol, and 15 g of soda previously dissolved in hydrated alcohol are mixed. The transesterification reaction is carried out while the mixture is being stirred at 30° C. After several minutes, the cloudy solution becomes homogeneous. After 2 hours, sampling of the solution is initiated, and it is determined by liquid phase chromatography (GPC: abbreviation of the English "Gel Permeation Chromatography") that the ester has a purity of 98%, with the remainder consisting of mono-, di- and triglycerides and sterol esters.

The absence of strong alkalis in the medium is verified before initiating a second stage, in which 300 g of glycerine that contains 5% by weight of alcohol and 5% by weight of water is added. The mixture of glycerine, ester, and alcohol is evaporated at atmospheric pressure in a distillation column, and 300 g of alcohol that titrates 95.3% is collected. At the beginning of the distillation, the alcohol that emerges is dry, and then it is increasingly hydrated. The temperature at the top of the distillation column is 78° C. and 120° C. at the bottom. The two phases that are formed are cooled to 75° C., and decanting is carried out. 620 g of glycerine phase (lower phase) and 895 g of ester phase (upper phase), which still contains dissolved alcohol, are obtained.

In a third stage, the ester phase is washed, and it is dried. 857 g of a dry ester which exhibits a purity that is close to that of the sample taken previously is obtained. The purity is 97.6%.

In a fourth stage, the glycerine phase is neutralized with 40 cm$^3$ of hydrochloric acid, and two phases, one glycerine (451 g) and the other consisting of a mixture of fatty acids and esters (209 g), are obtained. The separation between the "fatty acids+esters" fraction and the glycerine is thus ensured.

In a fifth stage, the transesterification or glycerolysis of the fatty acids and/or esters is carried out with glycerine by heating the "fatty acids+esters" fraction with neutralized glycerine and a basic unneutralized fraction of glycerine, by using as catalysts the soaps that are present in glycerine and that are catalysts at temperatures of above, for example, 170° C.

To optimize the yields, the fatty acids+esters that are obtained in two successive transesterifications are collected. Whereas in the first transesterification a commercial glycerine was used to bring about decantation, for the second batch of ester the neutralized glycerine that is obtained in the first reaction is used. In practice, 400 g of the ester+fatty acids phase that is obtained in the two reactions is heated with a mixture of 31 g of unneutralized basic glycerine that contains 0.75 g of potential soda in the form of soaps and 100 g of glycerine that is neutralized with hydrochloric acid to a pH of 6.

The 100 g of glycerine is obtained from a batch of 430 g of neutralized glycerine that is heated to 150° C. to dry it partially and from which 300 g is taken for the third stage and the third reaction.

Heating is done to 180–200° C. at atmospheric pressure. Several tens of grams of an alcohol-water mixture are withdrawn. After 3 hours of heating, the mixture, which exhibits an acid number of below 2, is titrated. The salts are filtered.

455 g of glycerides and 545 g of oil are subjected to transesterification as described hereinabove 860 g of ester is again obtained. The final yield is therefore, by weight relative to the oil, $(857+860+860)/(1000+1000+545)=101.5\%$.

The losses are mainly soaps and ester which, during filtration of the salt from the "esters+glycerides" phase, remain impregnated in the latter. Ester is also lost in washing the ester and in its purification. The yield is very satisfactory, however.

The ethyl esters that are obtained exhibit the following overall composition:

| | |
|---|---|
| ethyl esters: | 95.87% |
| monoglycerides: | 1.90% |
| diglycerides + sterol esters: | 2.06% |
| triglycerides: | 0.17% |
| alkalinity: | <5 ppm |

EXAMPLE 2

In this example, to demonstrate the effect of the amount of ethyl alcohol employed on the purity of the esters that are obtained, the procedure of Example 1 is repeated several times. In the various tests, amounts of ethyl alcohol at 95% by weight that range from 30 to 100 g are introduced successively into 100 g of sunflower seed oil. The amount of soda that is dissolved in the alcohol is 1.5 g.

At 30° C., a homogeneous phase is obtained at the end of one hour. The purity of the esters after the alcohol and the catalyst are eliminated is provided by the following table:

| Amount of alcohol (g) | MG* (% by weight) | DG* (% by weight) | TG* (% by weight) | EE* (% by weight) |
|---|---|---|---|---|
| 30 | 7.5 | 4.5 | 3.4 | 84.5 |
| 40 | 6.3 | 4.5 | 3.4 | 85.7 |
| 50 | 1.3 | 3.6 | 0.8 | 94.0 |
| 100 | 0.9 | 1.8 | 0.0 | 97.2 |

*MG = monoglycerides, DG = diglycerides + sterol esters, TG = triglycerides, EE = ethyl esters Good results are obtained for alcohol weights of 50 and 100 g.

EXAMPLE 3

In this example, the procedure of Example 1 is repeated several times, working with an alcohol/oil ratio by weight of 1, a soda concentration of 1.5% by weight relative to the oil, with stirring at the beginning of several minutes until a homogeneous phase is obtained, and then continuation of the reaction for 24 hours at 20° C. The water content of the ethyl alcohol used varies. The results are provided in the following table:

| Water in the alcohol (% by weight) | Stirring (minutes) | MG (% by weight) | DG (% by weight) | TG (% by weight) | EE (% by weight) |
|---|---|---|---|---|---|
| 3 | 0.6 | 1.20 | 1.8 | 0 | 97.0 |
| 5 | 3 | 1.0 | 1.8 | 0 | 97.2 |
| 8 | 5 | 1.3 | 2.1 | 0.4 | 96.2 |
| 10 | 8 | 3.4 | 4.4 | 13.1 | 79.0 |

It is thus demonstrated that when the amount of alcohol that is introduced is large relative to the oil, the transesterification reaction can be carried out with water contents in the alcohol that can be greater than 5% by weight.

EXAMPLE 4

Tests similar to those of Example 3, but with 50% by weight of ethyl alcohol relative to the oil, are carried out. The procedure is performed at 30° C. for 1 hour. The results are provided in the following table, which shows that lower performance levels are obtained.

| Water in the alcohol (% by weight) | MG (% by weight) | DG (% by weight) | TG (% by weight) | EE (% by weight) |
|---|---|---|---|---|
| 5 | 1.3 | 3.7 | 0.8 | 94 |
| 7 | 5.5 | 3.9 | 3.4 | 85 |
| 10 | 9.6 | 12.8 | 21 | 56.2 |

EXAMPLE 5

The procedure of Example 1 is repeated several times, varying the water content of the glycerine that is added after the transesterification reaction. The ethyl alcohol that is used exhibits an alcohol level of 95% by weight. The ethyl alcohol content of the alcohol that passes at the beginning of distillation and the final yield of ethyl esters are determined. The results are indicated in the following table:

| Water in the glycerine that is introduced (% by weight) | Alcohol content of the distilled alcohol (% by weight) | Yield of esters (% by weight) |
|---|---|---|
| 0 | 99.9 | 85.0 |
| 20 | 96.6 | 85.0 |
| 35 | 91.6 | 85.1 |
| 50 | 89.4 | 84.4 |

It appears that the yield by weight of esters does not depend significantly on the amount of water that is present in the glycerine added. In contrast, the latter affects the water content of the alcohol that is recovered at the beginning of distillation, even if an ethyl alcohol with 95% by weight is used.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

The entire disclosure of all applications, patents and publications, cited above, and of corresponding French application 96/05820, are hereby incorporated by reference.

What is claimed:

1. A process for the production of ethyl esters of fatty acids from a fatty acid glycerides starting substance selected from the group consisting of vegetable oil, animal oil, fat and or mixtures of glycerides, the process comprising the following stages: (a) transesterifying the fatty acid glyceride starting substance with hydrated ethyl alcohol at a temperature of 5 to 50° C. using an alkaline catalyst to form a medium comprising ethyl esters and excess ethyl alcohol said hydrated ethyl alcohol having an ethyl alcohol content of 92 to 99% by weight and being in a proportion of 30–100% by weight with respect to the starting substance; (b) adding a glycerine phase to said medium, and evaporating the excess ethyl alcohol to produce two immiscible phases, an ester phase and a glycerine phase A, and recycling said excess ethyl alcohol to stage (a), said excess ethyl alcohol having an ethyl alcohol content at least equal to the alcohol content of the hydrated ethyl alcohol used in step (a); (c) separating said glycerine phase A and said ester phase to obtain the desired ethyl esters; (d) neutralizing said glycerine phase A with acid, and separating resultant "fatty acids+ esters" phase and a glycerine phase B, and drying the latter phase; and (e) subjecting the "fatty acids+esters" phase to glycerolysis with at least a fraction of the dried glycerine phase B in the presence of an alkaline catalyst to form a mixture of glycerides and esters, and passing said mixture into transesterification stage (a).

2. A process according to claim 1, wherein, computed relative to the starting substance the alkaline catalyst corresponds to 1 to 2% by weight of soda to the fatty acid glyceride starting substance, and a proportion of 30 to 100% by weight of hydrated ethyl alcohol and a proportion of 30 to 100% by weight of hydrated ethyl alcohol.

3. A process according to claim 1, wherein the hydrated ethyl alcohol that is used exhibits an alcohol content of 94 to 97% by weight and is used at a proportion of 40 to 60% by weight relative to the starting oil.

4. A process according to claim 1, wherein the glycerine phase that is used in stage (b) is a fraction of glycerine phase B that is obtained in stage (d), dried to a temperature of about 150° C.

5. A process according to claim 4, wherein said glycerine phase contains 1 to 20% water and is used at a proportion of 20 to 40% relative to the starting oil.

6. A process according to claim 1, wherein the glycerolysis reaction of stage (e) is carried out at a temperature of 170 to 220° C., catalyzed with a fraction of basic glycerine phase A that is separated in stage (c) and is continued until a product is obtained whose acid number is less than 2.

7. A process according to claim 1, wherein the product that is obtained at the end of stage (e) is, after filtration, recycled to the oil, the fat, or the starting mixture of glycerides or to stage (a).

8. A process according to claim 5, wherein the glycerolysis reaction of stage (e) is carried out at a temperature of 170 to 220° C., catalyzed with a fraction of basic glycerine phase A that is separated in stage (c) and is continued until a product is obtained whose acid number is less than 2.

9. A process according to claim 8, wherein the product that is obtained at the end of stage (e) is, after filtration, recycled to the oil, the fat, or the starting mixture of glycerides or to stage (a).

10. A process according to claim 1, wherein said fatty acid glyceride starting substances are not subjected to any acidic transesterification step prior to step(a).

11. In a process for the production of ethyl esters of fatty acids from a starting substance selected from the group consisting of vegetable or animal oil fat, and mixtures of glycerides, the improvement comprising transesterifying the starting substance with a hydrated ethyl alcohol having a content of 92 to 99% by weight of ethyl alcohol, said hydrated ethyl alcohol being in a proportion of 30 to 100% by weight of ethyl alcohol with respect to the starting substance, said transesterifying being conducted in the presence of an alkaline catalyst and at a temperature of 5 to 50° C., evaporating the excess ethyl alcohol and separating the resultant glycerine and ethyl esters.

12. A process according to claim 11, wherein said fatty acid glyceride starting substances are not subjected to any acidic transesterification step prior to step(a).

13. A process according to claim 11, wherein, computed relative to the starting substance the alkaline catalyst corresponds to 1 to 2% by weight of soda to the fatty acid glyceride starting substance.

14. A process according to claim 11, wherein the hydrated ethyl alcohol that is used exhibits an alcohol content of 94 to 97% by weight and is used at a proportion of 40 to 60% by weight relative to the starting substance oil.

15. A process according to claim 11, wherein said transesterifying stage (a) is conducted at between 20° and 50° C.

16. A process according to claim 11, wherein said process consists essentially of said stages.

17. A process according to claim 1, wherein said alkaline catalyst is an alkaline alcoholate.

18. A process according to claim 11, wherein said alkaline catalyst is an alkaline alcoholate.

* * * * *